(12) United States Patent
Contino-Pepin et al.

(10) Patent No.: US 12,251,451 B2
(45) Date of Patent: Mar. 18, 2025

(54) EMULSION FOR ULTRASOUND ABLATION SURGERY

(71) Applicants: AVIGNON UNIVERSITE, Avignon (FR); CENTRE NATIONAL DE LA RECHERCHE SCIENTIFIQUE—CNRS, Paris (FR); INSTITUT NATIONAL DE LA SANTÉ ET DE LA RECHERCHE MÉDICALE, Paris (FR); SORBONNE UNIVERSITE, Paris (FR); UNIVERSITE DE MONTPELLIER, Montpellier (FR); ECOLE NATIONALE SUPERIEURE DE CHIMIE DE MONTPELLIER, Montpellier (FR)

(72) Inventors: Christiane Contino-Pepin, Althen des Paluds (FR); Stéphane Desgranges, Avignon (FR); Nicolas Taulier, Paris (FR)

(73) Assignees: Avignon Université, Avignon (FR); CENTRE NATIONAL DE LA RECHERCHE SCIENTIFIQUE—CNRS, Paris (FR); INSTITUT NATIONAL DE LA SANTÉ ET DE LA RECHERCHE MÉDICALE, Paris (FR); Sorbonne Université, Paris (FR); UNIVERSITE DE MONTPELLIER, Montpellier (FR); ECOLE NATIONALE SUPERIEURE DE CHIMIE DE MONTPELLIER, Montpellier (FR)

( * ) Notice: Subject to any disclaimer, the term of this patent is extended or adjusted under 35 U.S.C. 154(b) by 501 days.

(21) Appl. No.: 17/252,100

(22) PCT Filed: Jun. 14, 2019

(86) PCT No.: PCT/EP2019/065757
§ 371 (c)(1),
(2) Date: Dec. 14, 2020

(87) PCT Pub. No.: WO2019/238956
PCT Pub. Date: Dec. 19, 2019

(65) Prior Publication Data
US 2021/0252172 A1  Aug. 19, 2021

(30) Foreign Application Priority Data
Jun. 14, 2018  (FR) ...................... 1855237

(51) Int. Cl.
*A61K 49/18* (2006.01)
*A61K 9/00* (2006.01)
*A61K 49/10* (2006.01)
*A61N 7/00* (2006.01)

(52) U.S. Cl.
CPC ........ *A61K 49/1806* (2013.01); *A61K 9/0009* (2013.01); *A61K 9/0019* (2013.01); *A61K 49/10* (2013.01); *A61N 7/00* (2013.01)

(58) Field of Classification Search
CPC .. A61K 9/0009; A61K 49/1806; A61K 9/107; A61K 9/1075; A61K 9/0019; A61K 41/0052; A61K 49/10; A61K 31/025; A61P 35/00; A61N 7/00; A61N 7/02
See application file for complete search history.

(56) References Cited

U.S. PATENT DOCUMENTS

| 5,733,526 A | * | 3/1998 | Trevino | ............... A61K 9/0026 424/455 |
| 2006/0034770 A1 | * | 2/2006 | Schneider | ............ A61K 49/223 424/9.52 |

FOREIGN PATENT DOCUMENTS

| EP | 1839677 A1 | | 10/2007 | |
| EP | 3095806 A1 | | 11/2016 | |
| JP | 63060943 | * | 3/1988 | ............. A61K 49/00 |
| WO | 2017001686 A1 | | 1/2017 | |

OTHER PUBLICATIONS

Gherase, J. Chem. Phys., 2006, 125, 044906 . (Year: 2006).*
Razgulin et al., Carbohydrate Research, 2015, 406, p. 10-18. (Year: 2015).*
JP 63-060943, Mar. 1988 (English translation). (Year: 1988).*
Pavia et al., Makromol. Chem., 1992, 193, p. 2505 -2517. (Year: 1992).*
Astafyeva et al. "Perfluorocarbon nanodroplets stabilized by fluorinated surfactants: characterization and potentiality as theranostic agents" Journal of Materials Chemistry B, No. 3, p. 2892-2907; Jan. 14, 2015 (16 pages).
International Search Report issued in International Application No. PCT/EP2019/065757, mailed Sep. 12, 2019 (7 pages).
Written Opinion issued in International Application No. PCT/EP2019/065757; Dated Sep. 12, 2019 (6 pages).

* cited by examiner

*Primary Examiner* — Michael G. Hartley
*Assistant Examiner* — Leah H Schlientz
(74) *Attorney, Agent, or Firm* — Osha Bergman Watanabe & Burton LLP

(57) ABSTRACT

The present description relates to an injectable emulsion comprising an amphiphilic compound, a first phase comprising droplets including at least one perfluorocarbon compound and a second phase, which is aqueous. The droplets have a diameter $d_{4,3}$ of between 0.5 pm and 5.5 pm, and the at least one perfluorocarbon compound has a boiling point above 100° C. The present description also relates to methods comprising administering such an injectable emulsion in, for example, ultrasound ablation surgery (FIG. 3).

13 Claims, 4 Drawing Sheets

EMULSION FOR ULTRASOUND ABLATION SURGERY

TECHNICAL FIELD

The present description relates to an emulsion that is particularly suitable for use in ultrasound ablation surgery. The present description also relates to such an emulsion for use thereof as an improving agent in ultrasound ablation surgery and also to a process for producing such an emulsion.

BACKGROUND

Ultrasound ablation surgery is a therapeutic method based on the use of ultrasound beams focused on targeted organs which is being developed for numerous diseases: fibroma treatment, currently in clinical phase, treatment of eye diseases and treatment of breast, liver, kidney, prostate and brain cancers, currently in clinical test phase. Generally coupled to MM monitoring to guide the treatment, ultrasound ablation is a type of noninvasive surgery which avoids in particular infections and scars and enables better patient recovery after the procedure, and it would therefore be desirable to use this surgery routinely.

Ultrasound ablation consists in heating a diseased tissue by means of a focused ultrasound beam to the point of burning the tissue. Ultrasound ablation therefore requires high ultrasound intensities, of the order of several thousand $W/cm^2$, hence the generally used term HIFU (High Intensity Focused Ultrasound). In addition, the frequencies generally used in HIFU ablation surgery are greater than 1 MHz, and may reach about 10 MHz. In order to heat a precise part of the diseased tissue, focused transducers are used to focus the ultrasound beam. Before or after the focal point, the ultrasound beam is defocused, and has thus an energy that is lower than the focal point, but all the same remains very high. When the ultrasound beam defocuses toward tissues that are not very dense, the heat dissipates very quickly, but when the beam reaches a dense medium such as, for example, the vertebrae, bones usually accumulate the heat provided by the ultrasound beam and this results in burning of the bone.

An attempt of solution for avoiding these risks of collateral damage to healthy bones and tissues is to use lower ultrasound intensities. This becomes possible by performing the ultrasound ablation after intravenous or intra-arterial injection or direct injection into a tissue to be treated, of emulsions of perfluorocarbon (PFC) droplets, which accumulate in the tissue. Under the action of the ultrasound, the PFC compound contained in the core of the droplets may undergo a liquid-to-gas phase change which brings about conversion of the droplets into bubbles, which may then implode under the effect of cavitation. The cavitation phenomenon may significantly increase the temperature at a local level, in particular at the focal point of the ultrasound wave, which results in the destruction of the targeted tissues, via a cascade amplified ablation phenomenon. At the focal point, the formation of a cloud of bubbles may also block the propagation of the ultrasound wave in remote field zones. Thus, in the presence of these droplets, it is possible to use ultrasound waves of lower intensity to achieve a certain temperature locally, which sometimes makes it possible to limit collateral damage by avoiding heating of bone or other sensitive dense tissues before and/or after the focal point.

On the basis of this principle, the use of emulsions of perfluorocarbon droplets has been reported for a wide range of therapeutic applications, such as HIFU ablation, but also medical imaging, embolotherapy, targeted delivery of active ingredients, histotripsy, and optical aberration correction. However, a certain amount of confusion remains with regard to the insonification parameters to be adjusted to the nature of the PFC droplets introduced as improving agents for these applications. This is because the exact mechanism of action of heat transfer from the ultrasound wave to the medium to be treated is still poorly understood.

With regard to tumor ablation surgery, these emulsions of perfluorocarbon droplets are nanoemulsions, implying PFC nanodroplets having a size generally of between 100 nm and 300 nm. For example, document WO 2017/001686 A1 describes nanodroplets of this size, and also a size preferably of between 100 nm and 250 nm. These nanoemulsions are based on the effect of enhanced retention by tumor tissues so as to accumulate therein (EPR, for Enhanced Permeability Retention). However, nanoemulsions require high activation energies at physiological temperature, which leads to the use of intensities generally equivalent to several thousand $W/cm^2$, and of frequencies generally greater than 1 MHz. Thus, even using emulsions of PFC droplets, in particular during ablation treatment of deep tissues, the rapid attenuation of the ultrasound beam leads to the deposition of high energies before and after the focal point, causing severe side effects, such as healthy bone and tissue burns.

SUMMARY

In the present description and in the claims, the term "comprise" is synonymous with (means the same thing as) "include", "contain", and is inclusive or open and does not exclude other elements not described or represented. In addition, in the present description, the term "approximately" is synonymous with (means the same thing as) a margin 10% lower and/or higher than the respective value.

One of the objectives of the present description is to provide an emulsion suitable for use as an improving agent that may be exploited in ultrasound ablation surgery while at the same time being capable of avoiding side effects such as healthy bone and tissue burns.

According to a first aspect of the present description, such an objective is achieved by means of an emulsion comprising:
 a first phase comprising droplets including at least one perfluorocarbon compound; and
 a second phase, which is aqueous; and
 an amphiphilic compound;
 wherein the droplets have a diameter $d_{4,3}$ of between 0.5 μm and 5.5 μm; and
 wherein the at least one perfluorocarbon compound has a boiling point above 100° C.

In the present description and in the claims, the perfluorocarbon compound is also denoted by its acronym PFC.

In the present description and in the claims, the term "$d_{4,3}$" is intended to mean the De Brouckère mean diameter, namely the volume-weighted mean diameter of the emulsion droplets, measured at the time of use of the emulsion, for example when the emulsion is injected into the body of a patient. In the description and the claims, all the diameter $d_{4,3}$ values are measured using a dynamic light scattering instrument, and determined by the Mie theory, as described in the detailed description.

In the present description and in the claims, the term "diameter D10 of the droplets" is intended to mean the droplet diameter for which 90% of the total population of the droplets of the emulsion have a diameter greater than or equal to this value. Likewise, the term "D90" is intended to mean the droplet diameter for which 10% of the total population of droplets of the emulsion have a diameter greater than this value.

The inventors have noted with surprise that the features of such an emulsion make it particularly suitable, without side effects, as an improving agent that may be exploited in ultrasound ablation surgery.

Without wishing to be bound by a particular theory, the inventors have noted that an emulsion as defined in one or more embodiments of the present description may accentuate the thermal contrast between the tissue to be treated by ultrasound ablation and the structures at risk in a field near to and far from the focal point. In point of fact, even when the ultrasound energy is concentrated on the focal point, said energy, in the case of the prior art nanoemulsions, may also be deposited along the ultrasound wave beam, in front of or behind the focal point, and may cause severe side effects, such as healthy bone and tissue burns. However, this problem, by virtue of the lower energies deposited before and after the focal point by the emulsion of the present description, is overcome.

In the present description and in the claims, the "focal point" is intended to mean the point where an ultrasound wave beam is focused during an ultrasound ablation performed on a tissue to be treated after intravenous or intra-arterial injection of the emulsion or injection of the emulsion directly into the tissue to be treated.

In addition, the inventors have been able to observe, on a model tissue treated with an emulsion comprising droplets as defined in one or more embodiments of the present description, that an ultrasound ablation performed by focusing an ultrasound beam at the focal point may cause a minimal loss of heat deposit, of the order of approximately 5% or less. This weak attenuation of the thermal efficiency is evidence of a high droplet stability.

In addition, droplets having a diameter $d_{4,3}$ of between 0.5 μm and 5.5 μm makes it possible, in particular but not exclusively, to lower their ultrasound activation threshold in comparison to smaller droplets, such as nanodroplets having a size of less than 0.5 μm.

A $d_{4,3}$ of the droplets of greater than 6 μm could cause an obstruction of the blood capillaries. On the other hand, a $d_{4,3}$ of less than 6 μm makes it possible to render the droplets transpulmonary.

According to one or more embodiments, the diameter $d_{4,3}$ of the droplets is between 2 μm and 5.5 μm, for example between 3 μm and 5 μm. For example, the diameter $d_{4,3}$ of the droplets is between 3.5 μm and 4.5 μm. The diameter $d_{4,3}$ of the droplets may be between 2.0 μm and 3.5 μm, for example between 2.2 μm and 3.0 μm.

According to one or more embodiments, the diameter $d_{4,3}$ of the droplets is between 1.0 μm and 2.0 μm, for example between 1.2 μm and 1.9 μm. For example, the diameter $d_{4,3}$ of the droplets is between 1.4 μm and 1.8 μm.

According to alternative—yet combinable—embodiments, when the $d_{4,3}$ of the droplets is between 0.5 μm and 5.5 μm, the D90/D10 ratio may be between 1.5 and 5.5.

According to one or more embodiments, the concentration by volume of the first phase in the second phase is between 0.001% v/v and 10% v/v. For example, the concentration by volume is between 0.10% v/v and 2% v/v. In other examples, the concentration is between 0.10% v/v and 0.30% v/v.

According to one or more embodiments, the at least one perfluorocarbon compound has a boiling point above 100° C. and less than or equal to 160° C. For example, the boiling point of the at least one perfluorocarbon compound may be between 110° C. and 160° C., for example between 120° C. and 160° C., for example between 130° C. and 160° C., for example between 130° C. and 150° C.

The inventors have been able to note, during tests performed on tissue models exposed to ultrasound beams, that an emulsion comprising at least one perfluorocarbon compound having a boiling point above 100° C., and for example a boiling point of at least 130° C., brings about an even more satisfactory thermal contrast effect, in particular in terms of increase in temperature at the focal point.

Such temperatures could prevent any vaporization. However, even without vaporization, the high density of liquid perfluorocarbons allows them to store the acoustic energy received in order to convert it into heat, thereby resulting in a local increase in temperature. However, if vaporization is achieved, an improved droplet stability may then be obtained, by virtue of the reversibility of the process of vaporization of the droplets into gas bubbles in very short times, which offers better ultrasound ablation control, making it possible to more successfully accentuate the thermal contrast between the tissue to be treated and the healthy structures or tissues at risk in the near-field and far-field of the focal point. In particular, the risks of embolism may be reduced in this way, given that the bubbles formed are larger in size than the droplets subject to the ultrasound beams.

Furthermore, the droplets having survived the treatment may then be used for subsequent applications, for example in imaging, which may accompany ultrasound ablation, in order to more accurately guide the ultrasound ablation or for vectorization and controlled release of active ingredients.

According to one or more embodiments, the at least one perfluorocarbon compound is selected from the group comprising perfluorooctane, perfluorononane, perfluorodecalin, perfluorooctyl bromide (PFOB) and perfluoro-15-crown-5-ether (PFCE).

According to one or more embodiments, the at least one perfluorocarbon compound is selected from the group comprising perfluorodecalin, perfluorooctyl bromide (PFOB) and perfluoro-15-crown-5-ether (PFCE).

According to one or more embodiments, the at least one perfluorocarbon compound may be in the presence of one or more other perfluorocarbon compounds as defined above and also included in the first phase of the emulsion.

According to alternative but nevertheless combinable embodiments, when the droplets include a perfluorocarbon compound, the boiling point of which is between 130° C. and 150° C., the saturation vapor pressure of said perfluorocarbon compound may be between 0.1 kPa and 10 kPa.

According to one or more embodiments, the droplets are dispersed in the second phase, which is aqueous. According to one or more embodiments, the amphiphilic compound, which performs the function of a surfactant, may encapsulate the droplets while conferring stability thereon.

According to one or more embodiments described hereinafter, this stability may be further improved by selecting the amphiphilic compound from compounds that are particularly suitable for conferring stability on the droplets and/or other properties.

According to one or more embodiments, the amphiphilic compound comprises a dendrimer of Dendri-TAC type, such as those described in patent application EP3095806 A1. Dentri-TACs constitute a new class of amphiphilic compounds which have self-assembly properties and are highly modular, whether in terms of the hydrophobic tail or of the multiplication of the branches of the hydrophilic head.

According to one or more embodiments, the amphiphilic compound comprises an oligomer of $F_iTAC_n$ type.

The amphiphilic compounds of $F_iTAC_n$ type confer not only improved stability on the droplets, but also exhibit good biocompatibility.

The $F_iTAC_n$ compounds comprise a hydrophilic portion (or "polar head") comprising an oligomer of polyTRIS type, and a hydrophobic portion comprising a fluoroalkyl linear chain. Thus, n is the degree of oligomerization of the polyTRIS portion and i is the number of carbon atoms bearing fluorine atoms.

According to one or more embodiments, i is between 6 and 10.

According to one or more embodiments, when i is between 6 and 10, n is between 1 and 40, preferably between 4 and 30.

According to one or more embodiments, when i is 8, n is between 1 and 40, for example between 4 and 30.

According to one or more embodiments, the amphiphilic compound is selected from the group comprising $F_6TAC_7$, $F_6TAC_{92}$, $F_6TAC_{29}$, $F_8TAC_7$, $F_8TAC_3$ and $F_8TAC_{17}$.

According to one or more embodiments, it is possible to functionalize the droplets of the emulsion by variably introducing specific ligands onto the polar head of the surfactant, such as RGD peptides or glycosidic units (mannose, glucose, galactose, etc.), in order to give the droplets a specificity to the environment of the tumor or any other tissue that the surgery aims to eradicate.

According to a second aspect, the abovementioned objective, and also other advantages, are obtained by means of an emulsion for use as an improving agent in ultrasound ablation surgery, the emulsion comprising:
- a first phase comprising droplets including at least one perfluorocarbon compound having a boiling point above 100° C.;
- a second phase, which is aqueous; and
- an amphiphilic compound;

wherein the droplets have a diameter $d_{4,3}$ of between 0.5 µm and 5.5 µm.

According to one or more embodiments, the emulsion may comprise one or more features already presented above with reference to the embodiments of the emulsion. Thus, for example, the diameter $d_{4,3}$ of the droplets may be between 2 µm and 5.5 µm, for example between 3 µm and 5 µm. In other examples, the diameter $d_{4,3}$ of said droplets is between 3.5 µm and 4.5 µm. The diameter $d_{4,3}$ of the droplets may also be between, for example, 2.0 µm and 3.5 µm, for example between 2.2 µm and 3.0 µm.

According to one or more embodiments, the diameter $d_{4,3}$ of the droplets is between 1.0 µm and 2.0 µm, for example between 1.2 µm and 1.9 µm. For example, the diameter $d_{4,3}$ of the droplets is between 1.4 µm and 1.8 µm.

According to one or more embodiments, the concentration by volume of the first phase in the second phase is between 0.001% v/v and 10% v/v. For example, the concentration by volume of the first phase in the second phase is between 0.10% v/v and 2% v/v. In other examples, the concentration of the first phase in the second phase is between 0.10% v/v and 0.30% v/v.

These concentrations, for which satisfactory tissue lesions have been measured, improve the feasibility/biocompatibility in vivo.

According to one or more embodiments, the at least one perfluorocarbon compound may comprise at least one perfluorocarbon compound selected from the group comprising perfluorooctyl bromide (PFOB), perfluorohexane (PFH), perfluoropentane (PFP), perfluoro-15-crown-5-ether (PFCE), dodecafluoropentane, perfluoropropane, decafluorobutane (DFB) and octafluoropropane (OFP). Thus, PFOB (bp=142° C.) may be used as single PFC compound in the droplets, but not exclusively. According to other embodiments, PFC compounds having different characteristics (different vapor pressure, boiling point) may be combined.

In addition to the advantages detailed above, the use of a PFC compound selected from the group offers the possibility of being used with limited toxicity, given the chemical and biological stability of the carbon-fluorine bond and the absence of perfluorocarbon metabolization in the organism—no enzymatic system capable of metabolizing PFCs being known at the current time.

The emulsion according to one or more embodiments offers the possibility of depositing lower energies before and after the focal point and lower ultrasound frequencies than those commonly used in HIFU ablation surgery. Since the depth of ultrasound penetration into the organism is inversely proportional to the frequency, targets deeply anchored in the organism to be treated may thus be reached. In addition, the heating of the tissue to be treated may be focused on this tissue, without pre-focal or post-focal heating. In this way, it is possible to increase the localized heat deposit of the ultrasound wave, which makes it possible to reduce the time required for the tumor ablation, and to reduce the safety risks for the patient, by ensuring protection of the healthy tissues in the near-field and far-field of the ultrasound wave, while at the same time using lower energy than in the ultrasound ablation of the prior art.

According to one or more embodiments, the use comprises the transmission of a focused ultrasound beam applied on an ablation surgery target tissue.

According to one or more embodiments, the focused ultrasound beam is applied on at least one zone of the target tissue, said at least one zone comprising ultrasound beam focusing points.

The transmission of the ultrasound beam to a tissue to be eradicated may for example be performed in one or more zones of the tissue, it being possible for said zones to be repeatedly insonified. The term "zone" is intended for example to mean a circle with a diameter of between 0.5 mm and 10 mm, for example between 2 mm and 6 mm, and comprising several ultrasound beam focusing points, for example from 1 to 100 points, said focusing points being regularly spaced out from one another so as to form said circle delimiting the zone.

According to one or more embodiments, the at least one zone may thus be insonified by the ultrasound beam in pulsed mode and applied on this zone for a predetermined insonification time. The insonification of a zone may for example be performed for a period of between 0 and 100 s, for example between 20 and 40 s.

According to one or more embodiments, the predetermined insonification time of each point of the at least one zone may be regular, that is to say equal for each point, and between 50 and 100 ms, for example between 70 and 90 ms. These insonifications may be applied in one and the same point with a duty cycle of between 3% and 100% (continuous mode), for example of between 70% and 90%. In the case of these relatively long insonification times, it has proven to be the case that the energetic activation threshold of the droplets increases proportionally to the frequency used, over a frequency range extending, for example, from 0.5 MHz to 2 MHz.

According to one or more embodiments, it is also possible to measure a duty cycle corresponding to the insonification of a point of the zone over the total insonification time for the zone, which may for example be between 0 and 100%, for example between 1 and 10%. This duty cycle correlates directly with the number of points counted in a zone when the insonification time is equal at each point.

The inventors have been able to observe that, in the presence of an emulsion according to the present description, the repetition of pulses at the same focal point causes a minimal loss of heat deposit on a model tissue, for example of approximately 5%.

According to one or more embodiments, the use comprises the transmission of a focused ultrasound beam having a frequency between 500 kHz and 2 MHz, for example of between 600 kHz and 1.50 MHz. The frequency used may for example be between 600 kHz and 1.20 MHz.

According to one or more embodiments, the ultrasound beam transmitted to a zone of the tissue to be treated by ablation surgery has an intensity of between 0.05 W/cm$^2$ and 10 000 W/cm$^2$. For example, the intensity of the ultrasound beam applied on a zone of the tissue may be between 500 W/cm$^2$ and 1000 W/cm$^2$, for example between 650 W/cm$^2$ and 850 W/cm$^2$.

According to one or more embodiments, the use of the emulsion in ultrasound ablation surgery comprises the transmission of an ultrasound beam applied on highly vascularized organs.

Indeed, the emulsions of droplets according to one or more embodiments stand out in terms of a larger droplet size than the emulsions of droplets commonly used, for which the $d_{4,3}$ is less than 0.5 µm. In that respect, the emulsions according to one or more embodiments may be further exploited in ablation surgery on highly perfused tumors, for which the desired thermocoagulation is complicated by a heat-dissipating effect.

For example, the organs targeted by ultrasound ablation surgery involving an example of emulsion according to the present description may be selected from the group comprising the liver, spleen, kidneys, prostate, breasts and pancreas.

According to one or more embodiments, the use comprises monitoring, by MM or echography, of the emulsion in ultrasound ablation surgery, in order to guide the treatment.

According to a third aspect, the description concerns a process for producing the emulsion as defined by one or more of the embodiments indicated above, the process comprising:

providing an amphiphilic compound, a first phase comprising a perfluorocarbon compound, and an aqueous second phase;

mixing the amphiphilic compound, the first phase and the second phase;

cooling the mixture obtained;

homogenizing the mixture at low energy so as to obtain the emulsion according to one or more embodiments of the emulsion described above.

According to one or more embodiments, the mixture may be cooled to a temperature approximately equal to 0° C., for example by means of an ice bath.

In addition, the homogenization comprises the use of a homogenization device. This device has proved to be superior in comparison with processes using higher energies, and using for example a "bioblock scientific vibracell 75043, 13-mm diameter sonotrode" device. The inventors have indeed noted that this type of process leads to the undesirable formation of bimodal populations of droplets, of both nanometric order and micrometric order.

The embodiments described above are not exhaustive. In particular, it is understood that additional embodiments may be envisaged on the basis of various combinations of the embodiments explicitly described. Unless otherwise specified in the present description, it will be apparent to those skilled in the art that all the embodiments described above may be combined with one another. For example, unless otherwise specified, all the features of the embodiments described above, whether they refer to the emulsion or to the uses thereof, may be combined with or replaced by other features of other embodiments.

Embodiments according to the aspects referenced above and also additional advantages will emerge on reading the following detailed description and the appended claims.

DETAILED DESCRIPTION

Figure 1:
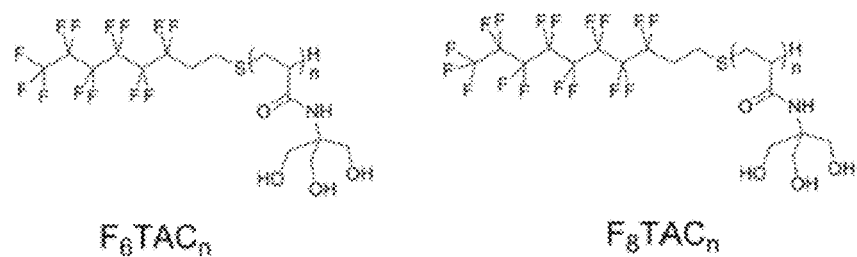
FIG. 1 is a representation of a molecular structure of a first and of a second example of amphiphilic compounds that may be used in emulsions according to embodiments of the present description.

In the following detailed description of the embodiments of the present invention, numerous specific details are disclosed in order to provide a fuller understanding of the present description. However, it will become apparent to those skilled in the art that the present description may be implemented without these specific details. In other cases, well-known characteristics have not been described in detail in order to avoid needlessly complicating the description.

Examples of emulsions 1-6 (see Table 2) according to embodiments of the present description are described below. Emulsions 1-6 use exemplary amphiphilic compounds, of F-TAC type, an example of a perfluorocarbon compound, namely perfluorooctyl bromide (PFOB), and also an example of a second phase, namely water. Emulsion 2, used as an example of an emulsion for use as an improving agent according to the present description, was introduced into tissues modeling target tissues in ultrasound ablation surgery. The results of the exposure of the model tissues loaded with emulsion 2 at various concentrations by volume are detailed below.

The description also gives an example of a process for producing emulsions 1-6.

1. Example of Synthesis of Amphiphilic Compounds

The surfactants of F-TAC type, used as examples of amphiphilic compounds, are synthesized by one-step radical polymerization according to a protocol described in the literature [Contino-Pepin et al., 2002, "Amphiphilic Oligomers: A New Kind of Macromolecular Carrier of Antimitotic Drugs. Curr. Med. Chem.—Anti-Cancer Agents", 2, 645-665]. Two types of perfluoroalkanethiols ($C_6F_{13}C_2H_4SH$ or $C_8F_{17}C_2H_4SH$, telogenic agents) and also azobisisobutyronitrile (AIBN) were used, respectively as transfer reagents and as radical initiator. 10 mL of solvent are used per gram of Tris-derived polymerizable monomer, namely tris(hydroxymethyl)acrylamidomethane (THAM; C=0.57 mol/L).

In a Schlenk tube under inert atmosphere, THAM (C=0.57 mol/L), a telogenic agent (introduced with a molar ratio $R_0$ as defined in Table 1 below) and AIBN (0.5 molar equivalent relative to the telogenic agent) are dissolved in freshly distilled methanol or in a mixture of methanol and water (9/1, v/v) for the preparation of F-TAC having high DPn values (DPn=n=degree of polymerization). After 3 freeze-thaw cycles under reduced pressure, the mixture is heated at 90° C. for 4 hours with stirring until the monomer has completely disappeared, followed by thin layer chromatography (TLC). The reaction crude is then precipitated twice from diethyl ether and filtered. The filtrate is then vacuum-dried and corresponds to the expected product (white powder, 32-84%, see Table 1 below). The DPn is evaluated by $^{19}F$ NMR, as previously described in Astafyeva, K. et al., 2015, "Perfluorocarbon nanodroplets stabilized by fluorinated surfactants: characterization and potentiality as theranostic agents" J. Mater. Chem. B, 3, 2892-2907.

TABLE 1

Polymerization conditions for various F-TACs
(where $R_0$ is the (telogenic agent)/(THAM) molar ratio)

|       | $F_6TAC_7$ | $F_6TAC_{12}$ | $F_6TAC_{29}$ | $F_8TAC_7$ | $F_8TAC_{12}$ | $F_8TAC_{18}$ |
|-------|------------|---------------|---------------|------------|---------------|---------------|
| $1/R_0$ | 4 | 12 | 20 | 4 | 8 | 12 |
| AIBN  | 0.5 | 0.5 | 0.5 | 0.5 | 0.5 | 0.5 |
| Yield | 63.4% | 81.3% | 31.8% | 65.2% | 84.0% | 65.1% |

2. Example of Process for Producing Emulsions 1-6

Exemplary emulsions 1-6, comprising the F-TACs of Table 1 and also an example of a PFC compound, namely PFOB, and also an example of a second phase, namely water, may be formed according to the general protocol below. The characteristics of these emulsions 1-6, such as the $d_{4,3}$ or the F-TAC used, are grouped together in Table 2.

Emulsions 1-6 are prepared with a Polytron® system PT 3100 homogenization device of the Kinematica brand.

The inventors carried out the following procedure in order to prepare an emulsion of droplets including PFOB and an F-TAC at 10% v/v: 835 mg (12.8 mg/ml of emulsion) of F-TAC surfactant are dissolved in 58.5 ml of distilled water using an ultrasound bath. 6.5 ml of PFOB are then added; the resulting mixture is cooled using an ice bath and the process for producing the emulsion is then initiated for three times 15 min using the Polytron® system PT 3100 at 22 500 RPM, with a pause of 30 min between each cycle in order to observe total disappearance of foam. The emulsion is then stored at 4° C. and diluted to the desired concentration before its use in ultrasound ablation surgery.

Determination of the Volume Fraction of PFC for Each Emulsion

The volume fraction of PFC for each emulsion 1-6 was evaluated after each preparation, using a known methodology based on $^{19}F$ NMR [Astafyeva, K. et al., 2015, "Perfluorocarbon nanodroplets stabilized by fluorinated surfactants: characterization and potentiality as theranostic agents" J. Mater. Chem. B, 3, 2892-2907]. The method was modified for the purpose of obtaining a totally homogeneous solution containing both the PFC compound and water. A mixture containing methanol and diethyl ether (50/50, v/v) was used for this purpose, in order to enable complete solubilization of the PFC compound.

Measurement of the $d_{4,3}$ of the Droplets for Each Emulsion

The size and also the size distribution among a population of droplets of each emulsion 1-6 are evaluated using a Mastersizer 2000 laser diffraction particle size analyzer (Malvern Instruments, Orsay, France) equipped with a Hydro2000S as sample dispersion unit (A), using a dynamic light scattering instrument. The refractive indices used for the PFOB and the dispersant (water) are respectively 1.305 and 1.333. Depending on the sample, a variable number of drops of emulsion is added to the sample dispersion unit (stirring 500 RPM) and the volume-weighted mean diameter $d_{4,3}$ (De Brouckère mean diameter) is determined by the Mie theory.

TABLE 2

Size and polydispersity of the droplets of emulsions 1-6

| Amphiphilic compound | $F_8TAC_7$ | $F_6TAC_7$ | $F_6TAC_{12}$ | $F_6TAC_{29}$ | $F_8TAC_{13}$ | $F_8TAC_{17}$ |
|----------------------|-----------|-----------|---------------|---------------|---------------|---------------|
| Emulsion | 1 | 2 | 3 | 4 | 5 | 6 |
| $d_{4,3}$ in μm | 4.07 ± 0.12 | 3.67 ± 0.17 | 1.48 ± 0.22 | 1.47 ± 0.09 | 0.62 ± 0.02 | 0.62 ± 0.09 |
| (D90/D10) | 4.84 | 4.00 | 2.90 | 2.00 | 3.97 | 3.30 |

3. Example of Ultrasound Beam Exposure of Model Tissues Loaded with Emulsion 2

Emulsion 2 comprising PFOB as first phase, water as second phase and the biocompatible amphiphilic compound $F_6TAC_7$ was used as an example of emulsion for use as an improving agent for ultrasound ablation surgery.

The examples of use of emulsion 2 were carried out on model tissues mimicking the acoustic properties of live soft tissues. The model tissues were uniformly loaded with emulsion 2, used at various concentrations by volume, and exposed to ultrasound beams.

Figure 2:
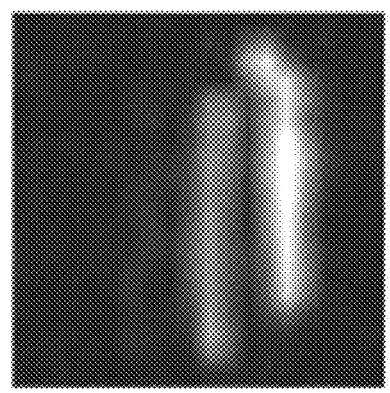
FIG. 2 shows a $^{19}$F MRI image of a model tissue treated with emulsions according to embodiments according to the present description.

The temperature increase of the model tissues exposed to ultrasound beams could be verified and compared to a control tissue not containing emulsion 2. The temperature increase through the model tissues was measured in real time, by PRSF (proton resonance shift frequency) magnetic resonance thermometry. This method makes it possible to obtain a precise return from the temperature chart at the focal point at high image number per second, and with millimetric resolution. The $^{19}F$ MRI imaging confirmed that the droplets of emulsion 2 were uniformly distributed through the model tissue for the two concentrations by volume tested, and also the absence of air bubbles (see FIG. 2).

Model Tissue Used

The model tissue, acoustically absorbent and composed in particular of agar-agar gel, was used for its capacity to reproduce acoustic properties very close to those of soft tissues, as for example attested to by Ramnarine, K., Anderson, T., Hoskins, P., 2001, Construction and geometric stability of physiological flow rate wall-less stenosis phantoms, ULTRASOUND Med. Biol. 27, 245-250. The composition of the agar gel used as model tissue is detailed in Table 3. It was in particular adjusted to the need to make it compatible with thermometry measurements, based on magnetic resonance imaging.

TABLE 3

Composition of the first model tissue

| Material | Glycerol | BAL | Agar | $SiO_2$ (1.5 µm) | $SiO_2$ (0.5 µm) | Water |
|---|---|---|---|---|---|---|
| Mass (g) | 33.6 | 0.27 | 9.0 | 2.85 | 2.64 | 251.6 |

The model tissue loaded with droplets has the same composition as the first model tissue described above, with the difference that the volume of emulsion introduced into the preparation replaces one and the same volume of water in order to achieve a constant final gel volume.

Influence of the Concentration by Volume of the Emulsion on the Thermal Improvement Effect The impact of the concentration of the example of emulsion 2 on the thermal improvement effect under exposure to ultrasound beams was measured. Two different concentrations of emulsion 2, namely 0.1% v/v and 0.5% v/v, were tested.

Figure 3:
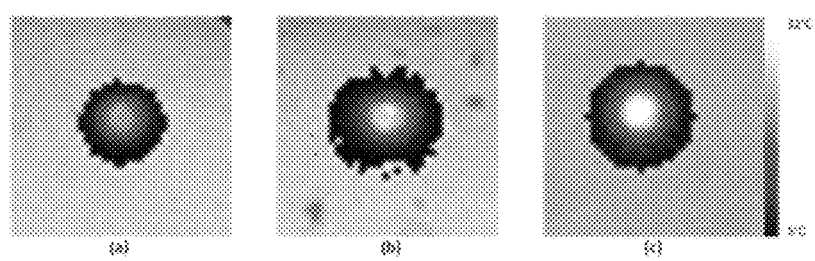
FIG. 3 shows a frontal view of a superimposition between an MM image of a model tissue loaded with emulsions according to embodiments of the present description, and a temperature chart obtained by thermometry during the exposure of the model tissue to an ultrasound beam, for various concentrations by volume of emulsions (a) (b) and (c), that is to say, respectively, 0% v/v, 0.1% v/v, 0.5% v/v.

FIG. 3 represents the superimposition of an MRI image of a model tissue and of the temperature chart at different concentrations by volume: 0.0% v/v, 0.1% v/v and 0.5% v/v. FIG. 3 makes it possible to observe that the surface area affected by the heat deposit is greater for the model tissue loaded with emulsion 2 than for the control model tissue (without emulsion 2), and that this surface area increases with the concentration by volume of PFOB droplets of emulsion 2.

Insonification Parameters

Focused Ultrasound Shot:

The ultrasound beam is transmitted to a zone of the target tissue of the ultrasound shot. The zone is delimited by 16 points at which the ultrasound beam is applied, all of the 16 points forming a circle 4 mm in diameter. The insonification of this zone lasts 1.65 s and covers the insonification of each point. Each point is insonified in pulsed mode over a period of 100 ms with a duty cycle of 70% or 90%. The insonification of the 16 points, corresponding to one complete turn of the circle, is repeated 20 times per shot, resulting in a total shot time of 33 s. The ultrasound beam has a frequency centered about 1 MHz and the acoustic power was adjusted to 94 W over the total ultrasound irradiation time, which corresponds to an intensity of 748 $W/cm^2$ of the ultrasound beam applied to the zone. Two duty cycles were tested, 70% and 90%, corresponding to pulse durations of 70 ms and 90 ms, respectively, over the range of 100 ms of insonification allotted to each point of the zone, per complete turn of the circle. This corresponds to a difference in delivered energy of 32% between the two assemblies, and to an equivalence of total insonification time for each point of 1.40 s and 1.80 s respectively, with a duty cycle over the total duration of the shot of 4.24% and 5.45%, respectively.

Figure 5:
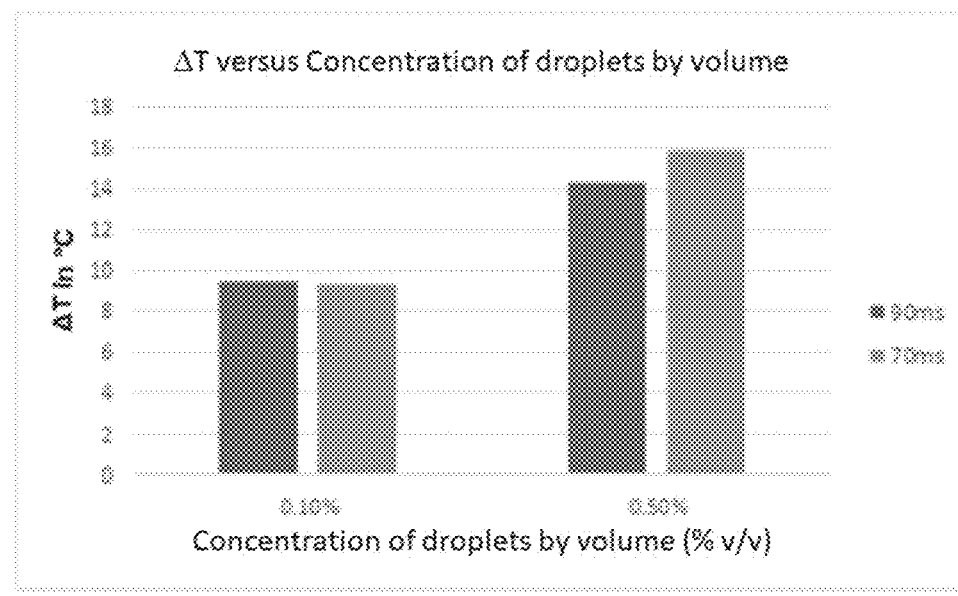
FIG. 5 shows the differences in heat deposit increase registered with respect to a control model tissue (without emulsion), for two different concentrations by volume of emulsions according to embodiments of the present description, and at two different duty cycles.

As shown in FIG. 5, under the two conditions, the results are similar with a heat efficiency compared to the shot performed on the control model tissue (without emulsion), of 9° C. and 15° C. for volume fractions of droplets of 0.1% v/v and 0.5% v/v, respectively.

Figure 4:
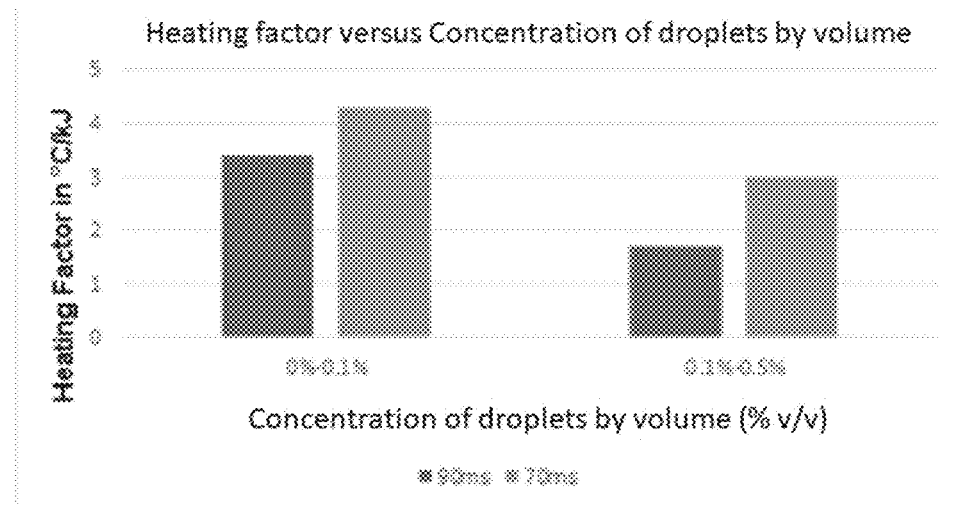
FIG. 4 shows the heating factor differences measured on model tissues loaded with emulsions according to embodiments of the present description, at different concentrations by volume and at two different duty cycles. Cases a) 0.1% v/v and 0% v/v; b) 0.5% v/v and 0.1% v/v are represented.

Heat Efficiency Measurement:

The differential heating factor reports, for each measurement, the increase in temperature relative to the control model tissue per unit of delivered energy (in kJ), and is calculated according to Formula 2, according to the respective heating factors of each gel (loaded or not loaded with droplets), calculated according to Formula 1:

Heating factor(° C./kJ)=[(temperature increase in ° C.)÷((total insonification time in seconds))× (Power in Watts))]        Formula (1):

Differential heating factor(° C./kJ)=Heating $factor_{loaded\ gel}$−Heating $factor_{blank\ gel}$        Formula (2):

The measurements of differential heating factor in the model tissues uniformly loaded with emulsion 2 according to the present description showed that the relationship between the concentration by volume of emulsion 2 and the generation of heat induced by exposure of the model tissue to an ultrasound beam is not linear. FIG. 4 clearly shows that the maximum increase in heating factor lies, for low concentrations by volume, between 0% v/v and 0.1% v/v.

Figure 6:
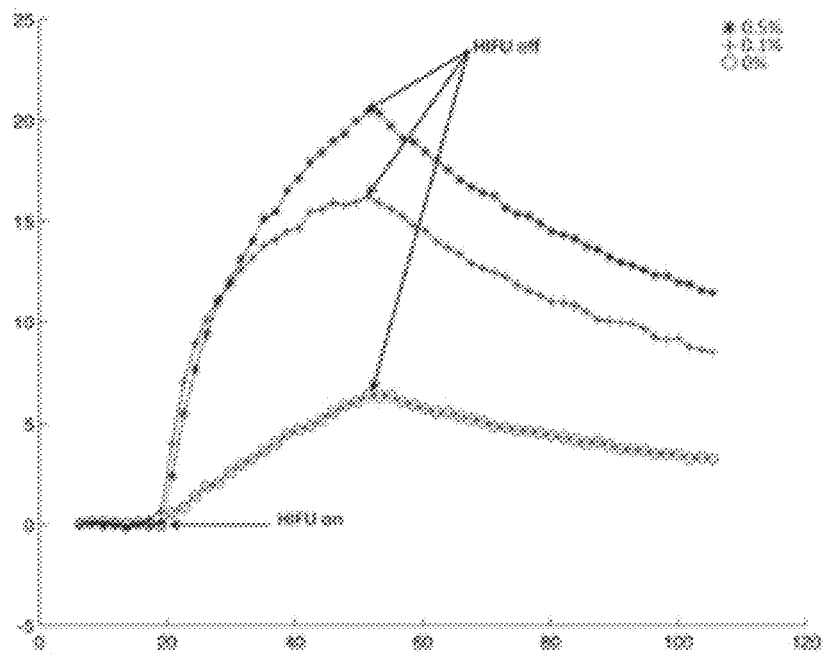
FIG. 6 shows the change in the temperature in model tissues loaded with emulsions according to embodiments of the present description, at various concentrations by volume of emulsions during the exposure of the model tissue to an ultrasound beam.

Evidence of the Possibility of Control in Surgery Provided by the Present Emulsions For each droplet concentration, the temperature continuously increases as long as the insonification lasts, but as soon as it is stopped, the temperature begins to decrease, as illustrated by FIG. 6. This is evidence of a possibility of additional control in ultrasound ablation surgery, provided by the emulsion according to the present description.

Figure 7:
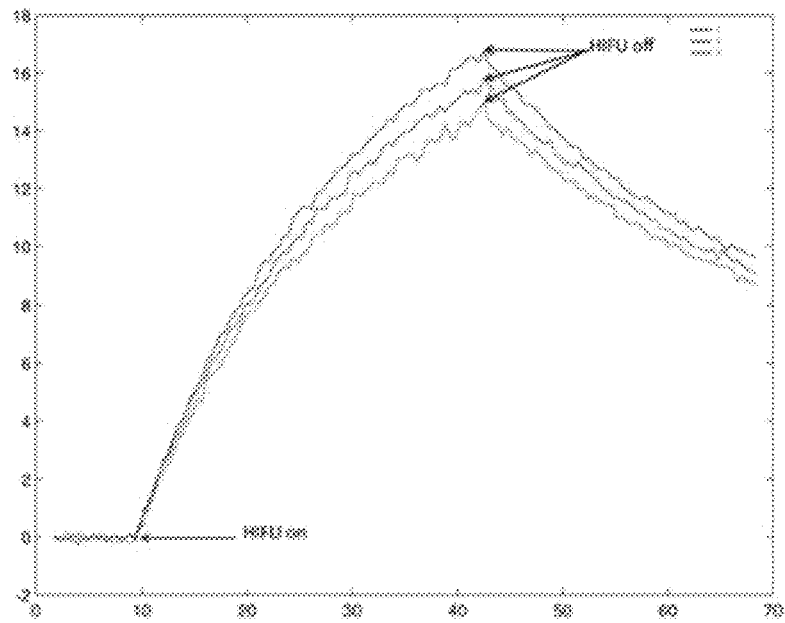
FIG. 7 shows the impact of the repetition of an exposure to ultrasound beams on the increase in temperature of the model tissue.

Likewise, FIG. 7 illustrates the fact that, contrary to the results of other research teams who observe a loss in heat efficiency of the droplets under exposure to ultrasound beams, the experimental results demonstrated the possibility of repeating the exposure to ultrasound beams with a minimal loss of 5% of gain in temperature. This droplet behavior confirms, if vaporization takes place, that the liquid to gas transition is reversible once the ultrasound irradiation is stopped.

Figure 8:
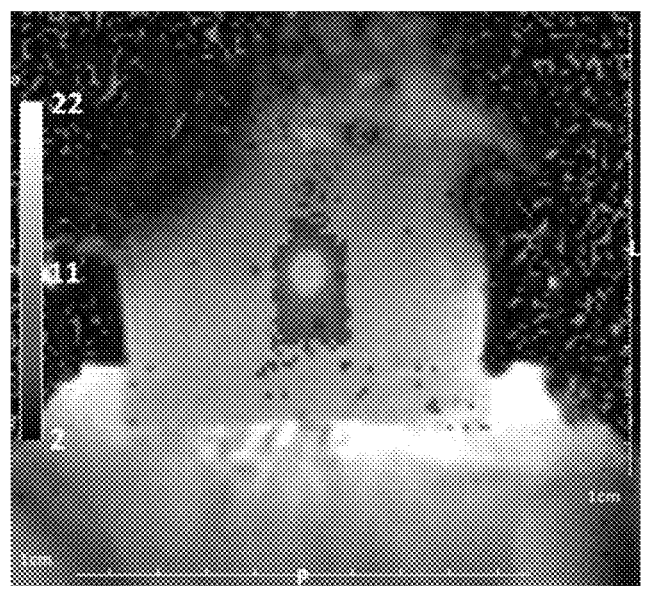
FIG. 8 shows a sagittal view of a superimposition between the MRI image of a model tissue loaded with emulsion according to one embodiment of the present description, at a concentration by volume of 0.5% v/v, and exposed to an ultrasound beam, and the temperature chart determined by thermometry.

Absence of Pre-Focal or Post-Focal Heating:

As shown in FIG. 8 by the cigar shape obtained after exposure of a model tissue to ultrasound beams according to the present description, the inventors noted that the use of an emulsion according to the present description did not result in pre-focal or post-focal heating.

The invention claimed is:

1. An injectable emulsion comprising:
   a first phase comprising droplets including at least one perfluorocarbon compound;
   a second phase, which is aqueous; and
   an amphiphilic compound;
   wherein the droplets have a diameter $d_{4,3}$ of between 1 μm and 5.5 μm;
   wherein the amphiphilic compound comprises a dendrimer of Dendri-TAC type;
   wherein a concentration by volume of the first phase in the second phase is between 0.001% v/v and 0.3% v/v; and
   wherein the at least one perfluorocarbon compound has a boiling point above 100° C.

2. The injectable emulsion of claim 1, wherein the at least one perfluorocarbon compound has a boiling point above 100° C. and below 160° C.

3. The injectable emulsion of claim 1, wherein the at least one perfluorocarbon compound is selected from the group consisting of perfluorooctane, perfluorononane, perfluorodecalin, perfluorooctyl bromide (PFOB) and perfluoro-15-crown-5-ether (PFCE).

4. A method for ultrasound ablation surgery, comprising:
   administering the injectable emulsion of claim 1 by intravenous or intra-arterial injection or direct injection into a tissue to be treated;
   transmitting a focused, ultrasound beam; and
   applying the focused ultrasound beam on at least one zone of the tissue.

5. A method of treating a cancer affecting an organ selected from the group consisting of the liver, spleen, kidneys, prostate, breasts and pancreas, the method comprising administering the injectable emulsion of claim 1 by intravenous or intra-arterial injection or direct injection into a tissue to be treated and performing ultrasound ablation thereafter.

6. A process for producing the injectable emulsion of claim 1, comprising:
   providing an amphiphilic compound, a first phase comprising a perfluorocarbon compound, and an aqueous second phase;
   mixing the amphiphilic compound, the first phase and the second phase;
   cooling the mixture obtained; and
   homogenizing the mixture at low energy so as to obtain the injectable emulsion of claim 1.

7. The method of claim 4, wherein the at least one zone of the tissue comprises focusing points of the focused ultrasound beam.

8. The method of claim 4, wherein transmitting is performed in pulsed mode and for a predetermined insonification time.

9. The method of claim 8, wherein applying is performed with a duty cycle corresponding to insonification of each focusing point of the at least one zone and comprised between 0 and 100%.

10. The method of claim 4, wherein the focused ultrasound beam has a frequency between 500 kHz and 2 MHz.

11. The method of claim 4, wherein the focused ultrasound beam has an intensity of between 0.05 W/cm$^2$ and 10 000 W/cm$^2$.

12. The method of claim 4, wherein applying is performed on highly vascularized organs.

13. The injectable emulsion of claim 1, wherein the at least one perfluorocarbon compound has a boiling point above 100° C. and below 160° C.

* * * * *